(12) United States Patent
Dyer et al.

(10) Patent No.: US 9,295,251 B1
(45) Date of Patent: *Mar. 29, 2016

(54) SYNERGISTIC ANTIMICROBIAL COMPOSITIONS OF PCMX AND CARBOXYLIC ACID AND RELATED METHODS

(71) Applicant: SAFEHANDS SOLUTIONS, LLC, Westborough, MA (US)

(72) Inventors: David Dyer, Cypress, CA (US); Jay Reubens, Boca Raton, FL (US)

(73) Assignee: SAFEHANDS SOLUTIONS, LLC, Oxford, MA (US)

( * ) Notice: Subject to any disclaimer, the term of this patent is extended or adjusted under 35 U.S.C. 154(b) by 347 days.

This patent is subject to a terminal disclaimer.

(21) Appl. No.: 13/932,048

(22) Filed: Jul. 1, 2013

Related U.S. Application Data

(63) Continuation-in-part of application No. 13/442,018, filed on Apr. 9, 2012, now Pat. No. 8,476,218.

(60) Provisional application No. 61/473,358, filed on Apr. 8, 2011.

(51) Int. Cl.

| | |
|---|---|
| *A01N 25/30* | (2006.01) |
| *A01N 31/10* | (2006.01) |
| *C11D 3/48* | (2006.01) |
| *A01N 31/08* | (2006.01) |
| *A01N 37/02* | (2006.01) |
| *A01N 37/10* | (2006.01) |
| *A01N 37/36* | (2006.01) |
| *A01N 37/40* | (2006.01) |

(52) U.S. Cl.
CPC ............... *A01N 31/08* (2013.01); *A01N 37/02* (2013.01); *A01N 37/10* (2013.01); *A01N 37/36* (2013.01); *A01N 37/40* (2013.01)

(58) Field of Classification Search
USPC .......... 510/386, 131, 518, 132; 424/400, 405
See application file for complete search history.

(56) References Cited

U.S. PATENT DOCUMENTS

| | | | |
|---|---|---|---|
| 2,577,773 | A | 12/1951 | Lambert |
| 3,419,006 | A | 12/1968 | King |
| 3,968,246 | A | 7/1976 | Merianos et al. |
| 4,203,872 | A | 5/1980 | Flanagan |
| 4,278,664 | A | 7/1981 | Van Cleave |
| 4,321,277 | A | 3/1982 | Saurino |
| 4,336,151 | A | 6/1982 | Like et al. |
| 4,533,351 | A | 8/1985 | Washkuhn |
| 4,657,758 | A | 4/1987 | Goldemberg et al. |
| 4,721,724 | A | 1/1988 | Stettendorf |
| 4,723,950 | A | 2/1988 | Lee |
| 4,797,420 | A | 1/1989 | Bryant |
| 4,931,282 | A | 6/1990 | Asmus et al. |
| 5,063,049 | A | 11/1991 | Billings |
| 5,114,978 | A | 5/1992 | Corti et al. |
| 5,181,914 | A | 1/1993 | Zook |
| 5,270,358 | A | 12/1993 | Asmus |
| 5,284,833 | A | 2/1994 | McAnalley et al. |
| 5,302,392 | A | 4/1994 | Karakelle et al. |
| 5,334,388 | A | 8/1994 | Hoang et al. |
| 5,346,692 | A | 9/1994 | Wohlrab et al. |
| 5,362,422 | A | 11/1994 | Masters |
| 5,439,681 | A | 8/1995 | Khan et al. |
| 5,439,682 | A | 8/1995 | Wivell et al. |
| 5,512,199 | A | 4/1996 | Khan et al. |
| 5,550,163 | A | 8/1996 | Ding et al. |
| 5,607,699 | A | 3/1997 | Hoang et al. |
| 5,629,006 | A | 5/1997 | Hoang et al. |
| 5,661,170 | A | 8/1997 | Chodosh |
| 5,698,475 | A | 12/1997 | Vlashbom |
| 5,705,532 | A | 1/1998 | Modak et al. |
| 5,708,023 | A | 1/1998 | Modak et al. |
| 5,736,058 | A | 4/1998 | Wright et al. |
| 5,837,274 | A | 11/1998 | Shick et al. |
| 5,908,865 | A | 6/1999 | Doi et al. |
| 5,951,993 | A | 9/1999 | Scholz et al. |
| 5,968,852 | A | 10/1999 | Vlashblom |
| 5,968,986 | A | 10/1999 | Dyer |
| 5,980,925 | A | 11/1999 | Jampani et al. |
| 5,985,931 | A | 11/1999 | Modak et al. |
| 5,994,383 | A | 11/1999 | Dyer et al. |
| 6,013,677 | A | 1/2000 | Dyer et al. |
| 6,022,549 | A | 2/2000 | Dyer |
| 6,022,551 | A | 2/2000 | Jampani et al. |
| 6,066,606 | A | 5/2000 | Lu et al. |
| 6,066,674 | A | 5/2000 | Hioki et al. |
| 6,087,400 | A | 7/2000 | Dyer et al. |
| 6,090,395 | A | 7/2000 | Asmus et al. |
| 6,110,381 | A | 8/2000 | Wright |
| 6,200,582 | B1 | 3/2001 | Iwamoto et al. |
| 6,241,898 | B1 | 6/2001 | Wright et al. |
| 6,242,486 | B1 | 6/2001 | Thornton et al. |

(Continued)

OTHER PUBLICATIONS

Dyer et al., Testing a New Alcohol-Free Hand Sanitizer to Combat Infection, Aorn Journal, Aug. 1998, vol. 68, No. 2.

Uniqema Personal Care, Phospholipids—A Natural Choice for Personal Care, Business Briefing: Global Cosmetics Manufacturing 2004.

Dyer et al., Measuring Skin Antibacterial Activity Skin Drying and Dermal Tolerance, Mar. 9, 2006, The Glove Juice Human Subject Independent Study (per FDA protocol at California State University-Fresno).

Lonza, Uniquat QAC.

Federal Register, Topical Antimicrobial Drug Products for over-the counter human use; Tentative final monograph for first aid antiseptic drug products, vol. 56, No. 140, Monday, Jul. 22, 1991.

(Continued)

*Primary Examiner* — Savitha Rao

(74) *Attorney, Agent, or Firm* — Allen, Dyer, Doppelt, Milbrath & Gilchrist, P.A.

(57) ABSTRACT

Antimicrobial compositions including PCMX and carboxylic acid and related methods are described. In a preferred embodiment, an antimicrobial composition comprises an enhanced synergistically effective antimicrobial mixture of PCMX, carboxylic acid, glycerol, isopropanol, and sodium dodecyl sulfate.

3 Claims, No Drawings

(56) References Cited

U.S. PATENT DOCUMENTS

| | | |
|---|---|---|
| 6,248,343 B1 | 6/2001 | Jampani et al. |
| 6,350,251 B1 | 2/2002 | Prosl et al. |
| 6,413,921 B1 | 7/2002 | Childers et al. |
| 6,479,039 B1 | 11/2002 | Dyer et al. |
| 6,503,952 B2 | 1/2003 | Modak et al. |
| 6,534,069 B1 | 3/2003 | Asmus et al. |
| 6,723,689 B1 | 4/2004 | Hoang et al. |
| 6,846,846 B2 | 1/2005 | Modak et al. |
| 7,005,031 B2 | 2/2006 | Lucast et al. |
| 7,144,846 B2 | 12/2006 | Keller et al. |
| 7,179,849 B2 | 2/2007 | Terry |
| 7,199,090 B2 | 4/2007 | Koivisto |
| 7,244,418 B2 | 7/2007 | Dyer et al. |
| 7,262,222 B2 | 8/2007 | Carlson et al. |
| 7,288,513 B2 | 10/2007 | Taylor et al. |
| 7,517,842 B2 | 4/2009 | Barnhart et al. |
| 7,607,442 B2 | 10/2009 | Barnhill et al. |
| 7,607,443 B2 | 10/2009 | Barnhill et al. |
| 7,617,830 B2 | 11/2009 | Barnhill et al. |
| 7,641,740 B2 | 1/2010 | Barnhill et al. |
| 7,651,990 B2 | 1/2010 | Asmus |
| 7,659,824 B2 | 2/2010 | Prodanovich et al. |
| 7,678,578 B2 | 3/2010 | Van Agthoven et al. |
| 7,682,464 B2 | 3/2010 | Glenn et al. |
| 7,683,018 B2 | 3/2010 | Koivisto et al. |
| 7,698,770 B2 | 4/2010 | Barnhill et al. |
| 7,745,425 B2 | 6/2010 | Modak et al. |
| 7,754,021 B2 | 7/2010 | Barnhill et al. |
| 7,754,022 B2 | 7/2010 | Barnhill et al. |
| 7,757,700 B2 | 7/2010 | Barnhill et al. |
| 7,758,701 B2 | 7/2010 | Barnhill et al. |
| 7,789,095 B2 | 9/2010 | Barnhill et al. |
| 7,803,390 B2 | 9/2010 | Asmus et al. |
| 7,818,083 B2 | 10/2010 | Glenn et al. |
| 7,883,585 B2 | 2/2011 | Barnhill et al. |
| 8,188,006 B2 | 5/2012 | Leeper et al. |
| 8,193,244 B1 | 6/2012 | Stockel et al. |
| 2001/0010016 A1 | 7/2001 | Modak et al. |
| 2001/0016589 A1 | 8/2001 | Modak et al. |
| 2003/0152644 A1 | 8/2003 | Modak et al. |
| 2003/0175503 A1 | 9/2003 | Lucast et al. |
| 2003/0212005 A1 | 11/2003 | Petito et al. |
| 2004/0219227 A1 | 11/2004 | Modak et al. |
| 2004/0247655 A1 | 12/2004 | Asmus et al. |
| 2005/0003991 A1 | 1/2005 | MacQuarrie |
| 2005/0013836 A1 | 1/2005 | Raad |
| 2005/0042266 A1 | 2/2005 | Narang |
| 2005/0129626 A1 | 6/2005 | Koivisto et al. |
| 2005/0192547 A1 | 9/2005 | Modak et al. |
| 2005/0238602 A1 | 10/2005 | Modak et al. |
| 2005/0249791 A1 | 11/2005 | Hobbs et al. |
| 2005/0260243 A1 | 11/2005 | Lynch et al. |
| 2006/0234894 A1 | 10/2006 | Taylor et al. |
| 2006/0281663 A1 | 12/2006 | Asmus |
| 2007/0020342 A1 | 1/2007 | Modak et al. |
| 2007/0027055 A1 | 2/2007 | Koivisto et al. |
| 2007/0048345 A1 | 3/2007 | Huang et al. |
| 2007/0065383 A1 | 3/2007 | Fernandez de Castro et al. |
| 2007/0087744 A1 | 4/2007 | Haglund |
| 2007/0179207 A1 | 8/2007 | Fernandez de Castro et al. |
| 2007/0202177 A1 | 8/2007 | Hoang |
| 2007/0258911 A1 | 11/2007 | Fernandez de Castro et al. |
| 2008/0113892 A1 | 5/2008 | Barnhart et al. |
| 2008/0247960 A1 | 10/2008 | Yuan |
| 2008/0255014 A1 | 10/2008 | Luu et al. |
| 2008/0312327 A1 | 12/2008 | Rypkema et al. |
| 2009/0111780 A1 | 4/2009 | Giordano |
| 2009/0187130 A1 | 7/2009 | Asmus et al. |
| 2010/0003198 A1 | 1/2010 | Stolmeier et al. |
| 2010/0189808 A1 | 7/2010 | Gupta et al. |
| 2010/0191219 A1 | 7/2010 | Gupta et al. |
| 2010/0239629 A1 | 9/2010 | Narayanan et al. |
| 2010/0260691 A1 | 10/2010 | Narayanan et al. |
| 2010/0263793 A1 | 10/2010 | Ylitalo et al. |
| 2010/0305211 A1 | 12/2010 | Modak et al. |
| 2010/0330195 A1 | 12/2010 | Cueman et al. |
| 2010/0331411 A1 | 12/2010 | Asmus |

OTHER PUBLICATIONS

SafeHands Points to the Dangers of Alcohol-Based Hand Sanitizers, Feb. 6, 2009, www.infectioncontrol today.

Quaternary Ammonium Chloride, Lonza Inc, Allendale, NJ, USA.

Uniqema Person Care, Phospholipids—A Natural Choice for Personal Care, Business Briefing: Global Cosmetics Manufacturing, 2004, pp. 1-6.

Dyer, Measuring Skin Antibacterial Activity Skin Drying and Dermal Tolerance, Alcohol-Based vs Alcohol Free Instant Hand Sanitizers, The Glove Juice Human Subject Independent Study, Mar. 9, 2006,pp. 1-11, California State University, Fresno.

Dyer, Testing New Alcohol-Free Hand Sanitizer to Combat Infection, AORN Journal, Aug. 1998, vol. 68, No. 2, pp. 239-251, Denver CO,USA.

SYNERGISTIC ANTIMICROBIAL COMPOSITIONS OF PCMX AND CARBOXYLIC ACID AND RELATED METHODS

CROSS-REFERENCE TO RELATED APPLICATIONS

This is a continuation-in-part of application Ser. No. 13/442,018, filed Apr. 9, 2012 and entitled "Antimicrobial Compositions and Related Methods," which claims priority to provisional Application No. 61/473,358, filed Apr. 8, 2011 and entitled "Antimicrobial Compositions and Related Methods." The entire contents of both of these applications are hereby incorporated by reference.

FIELD OF THE INVENTION

The invention relates to the field of antimicrobial compositions, and, more particularly to antimicrobial compositions comprising parachlorometaxylenol ("PCMX").

BACKGROUND

Although hand washing limits the spread of microorganisms that cause illness, immediate access to soap and water, and the lack of time needed to correctly wash hands present significant barriers to implementing rigorous hand washing policies in the workplace, especially for workers on manufacturing floors. Instant hand sanitizers can be of great use in situations where soap and water are not available for regular hand washing. Studies have shown that illness absenteeism associated with transmissible pathogens is decreased by 15-50% when rinse free instant hand sanitizers are routinely used. Therefore, using instant hand sanitizers in the workplace can save a company millions of dollars annually.

Commercially available instant hand sanitizers can be grouped into two categories: alcohol-free and alcohol-containing. Of the former category, quaternary ammonium compounds are most frequently employed as the antimicrobial active ingredient. Of the latter category, ethanol at a concentration range of 62-70% w/w is most prominent on the market. Both alcohol-free and alcohol-containing products generally are equally effective at reducing germs on the skin with a single use. With repeated use alcohol-free products show a significant persistence of antimicrobial activity whereas alcohol-containing products appear to increase the skin's ability to carry pathogens.

Microorganisms that spread from human skin can adversely affect electronic components when the workers in the electronics manufacturing facility contact the electronic components. Some microorganisms pose a danger to electronic-component materials because they can destroy metal alloys, electric contacts, and various polymers. In a study of long-term manned spaceflight missions, more than 100 species of microorganisms were identified on the surfaces of materials (bacteria and fungi). Among them were pathogenic ones such as saprophytes capable of active growth on artificial substrates, as well as technophilic bacteria and fungi. Such biotic contaminants can degrade and destroy metals and polymers, disrupting the functionality of the electronic equipment.

In a typical electronics manufacturing process, it is imperative to avoid contaminating electronic components as they are processed. Some chemical contaminants will prevent solder wetting by forming a barrier between flux and the oxides. Others present a physical barrier to the flow of electricity after assembly (grease on gold contacts, for example). Ionic contamination can originate as the vestiges of the acids used to remove oxides, and as other ionic compounds introduced incidentally from workers' hands into circuitry.

SUMMARY

In view of the foregoing it is an object of the invention to provide a composition that reduces or eliminates microbes on the skin and also minimizes the potential of contaminating sensitive electronic components.

A composition aspect of the invention that achieves this objective is an antimicrobial composition that comprises an enhanced synergistically effective antimicrobial mixture of PCMX, carboxylic acid, glycerol, isopropanol, and sodium dodecyl sulfate.

In a method aspect of the invention, a method of preventing interference with electronic components from residue of an electronics worker's hands comprises topically treating the electronics worker's hands with an amine-free enhanced synergistically effective antimicrobial mixture of PCMX, carboxylic acid, glycerol, isopropanol, and sodium dodecyl sulfate and, subsequently, grasping the electronic components with the treated hands.

In another method aspect of the invention, a method of increasing the antimicrobial effectiveness of an amine-free sanitizing solution having PCMX as an antimicrobial active ingredient comprises blending a carboxylic acid with the amine-free sanitizing solution having PCMX as an antimicrobial active ingredient to a ratio of about 30:1 to about 3:1 of PCMX:carboxylic acid, wherein the carboxylic acid synergizes with PCMX in such a way that the antimicrobial effectiveness of the PCMX and carboxylic acid blend is enhanced relative to the sum of antimicrobial effectiveness measurements of PCMX and carboxylic acid when one is measured in the absence of the other.

These and other objects, aspects, and advantages of the present invention will be better appreciated in view of the following detailed description of preferred embodiments.

DETAILED DESCRIPTION PREFERRED EMBODIMENTS

In the Summary above and in the Detailed Description of Preferred Embodiments, reference is made to particular features (including method steps) of the invention. It is to be understood that the disclosure of the invention in this specification includes all possible combinations of such particular features. For example, where a particular feature is disclosed in the context of a particular aspect or embodiment of the invention, that feature can also be used, to the extent possible, in combination with and/or in the context of other particular aspects and embodiments of the invention, and in the invention generally.

The term "comprises" is used herein to mean that other ingredients, features, steps, etc. are optionally present. When reference is made herein to a method comprising two or more defined steps, the steps can be carried in any order or simultaneously (except where the context excludes that possibility), and the method can include one or more steps which are carried out before any of the defined steps, between two of the defined steps, or after all of the defined steps (except where the context excludes that possibility).

In this section, the invention will be described more fully with reference to certain preferred embodiments. This invention may, however, be embodied in many different forms and should not be construed as limited to the embodiments set forth herein.

Chemicals that pose a high risk of interfering with electronic components include amines or ammonium compounds, silicon-based compounds, and terpenes. Accordingly, preferred embodiments of the antimicrobial composition are amine-free, meaning that they do not contain amines of any form, including ammonium compounds.

PCMX is desirable for use as an antimicrobial active ingredient in rinse-free hand sanitizer compositions due to the fact that it is unlikely to interfere with electronic circuitry at concentrations resulting from incidental contact from workers' hands. Unfortunately, however, PCMX-based hand sanitizers are difficult to prepare because PCMX is incompatible with many conventional surfactants. Besides this, PCMX also has the tendency to interact with other ingredients and have pH and solubility limitations that can adversely affect PCMX's antimicrobial effectiveness.

Parachlorometaxylenol ("PCMX") is a phenolic compound that is effective against both gram-positive and gram-negative bacteria. PCMX is sometimes referred to by its other names, including: chloroxylenol; 4-chloro-3,5 xylenol; 4-chloro-3,5-dimethylphenol; 2-chloro-m-xylenol; 2-chloro-5-hydroxy-m-xylene; 2-chloro-5-hydroxy-m-xylene; 2-chloro-5-hydroxy-1,3-dimethylbenzene; 4-chlor-1-hydroxy-3,5-dimethyl benzene; and 3,5-dimethyl-4-chlorophenol.

Preferred embodiments of the antimicrobial compositions are useful as rinse-free instant hand sanitizers. These embodiments are particularly advantageous for use by workers in the electronics industry to decrease the likelihood of contaminating components resulting from incidental contact. Preferably, the antimicrobial compositions do not contain chemical components that will interfere with the assembly or proper function of electronic circuitry and hardware at concentrations anticipated from incidental contact from a worker's hands.

Antimicrobial compositions according to embodiments of the invention comprise a combination of parachlorometaxylenol (PCMX) and other optional ingredients, including surfactants, co-solvents and emollients which will provide an instant hand sanitizer with significant antimicrobial activity against a broad spectrum of pathogens, including gram-positive and gram-negative bacteria, yeasts, molds fungi and viruses, and that is amenable to frequent use on human hands, and whose excipients are compatible with the chemical constraints of the electronics manufacturing industries.

The inventors unexpectedly discovered that PCMX and carboxylic acids can be blended to produce an enhanced synergistically effective antimicrobial mixture, which shows an enhanced measurement of antimicrobial effectiveness relative to the combined measurements of antimicrobial effectiveness of PCMX and the carboxylic acids when tested individually in the absence of the other. Both PCMX and certain carboxylic acids have their own individual antimicrobial effectiveness values when tested in the absence of the other. When mixed together, however, the antimicrobial effectiveness of the mixture is greater than the sum of their individual antimicrobial effectiveness values.

Preferred concentrations of the various ingredients will now be discussed with respect to % w/w, which refers to the percent, by weight, of each ingredient relative to the total weight of the composition.

The preferred antimicrobial active ingredient, PCMX, is present in the composition at a concentration that is synergistically antimicrobially effective when blended with a carboxylic acid. In some preferred embodiments, the composition includes about 0.1% w/w to about 3.0% w/w PCMX, about 1% w/w to about 3% w/w PCMX, and, more preferably, about 1.5% w/w to about 2.5% w/w PCMX.

Preferably, the PCMX is blended with one or more carboxylic acids that pose little risk of depositing residue on electronic components. The carboxylic acids are selected from a wide variety of organic molecules containing carboxylic acid functional groups.

Particularly preferred carboxylic acids include benzoic acid, citric acid, acetic acid, salicylic acid, and combinations thereof. The concentration of carboxylic acids in preferred embodiments is from about 0.1% w/w to about 0.5% w/w, about 0.1% w/w to about 0.3% w/w, or about 0.15% w/w to about 0.25% w/w.

The antimicrobial composition also includes one or more anionic surfactants to help solubilize PCMX and preserve its antimicrobial activity. Preferred anionic surfactants include, but are not limited to, sodium salts of n-alkyl sulfates such as sodium dodecyl sufate, ethoxylated alkyl sulfates, and sarcosine surfactant. In certain embodiments, anionic surfactants in the composition collectively comprise about 0.5 to about 3% w/w, about 0.75% w/w to about 2.5% w/w, or about 1.5% w/w to about 2.5% w/w.

The antimicrobial composition may further comprise a bridging surfactant that also enhances the solubility of PCMX and preserves its antimicrobial activity. A preferred bridging surfactant is poly(oxyethylene)20 cetyl ether, which has a calculated HLB value of 15.7 on a hydrophilic-lipophilic scale (HLB) of 0-20, in which 20 is very hydrophilic (polar), and which has a critical micelle concentration (CMC) of 0.007 mM to 0.077 mM. Preferred concentrations of the bridging surfactant are about 0.01% w/w to about 1.5% w/w or about 0.2% w/w to about 0.5% w/w.

Some embodiments of the antimicrobial composition also include excipients that are used to moderate the effect of anionic surfactants on the skin. A variety of conventional excipients may be used for this purpose. In one particular embodiment, this excipient is glycerol. Such excipients are present in a concentration of about 0.01% w/w to about 0.2% w/w, about 0.05% w/w to about 1.5% w/w, or about 0.01% w/w to about 0.05% w/w.

Additionally, anionic sulfonate surfactants may be employed if desired. For example, sodium pareth C12-15 sulfonate may be present in a preferred concentration range of about 0.01% w/w to about 2% w/w, 0.05% w/w to about 1.5% w/w, or about 1.0% w/w to about 1.25% w/w.

The antimicrobial composition may also include other ingredients such as preservatives, emulsifiers, foaming agents, fragrances, and colors among others. Suitable preservatives include those that are used in cosmetics. A particularly preferred preservative is phenoxyethanol present in an amount of about 0.001% w/w to about 0.5% w/w.

The solvent(s) used in the antimicrobial composition should be compatible with electronic components. Solvents that can be used include water and alcohols and/or glycols. Alcohols and glycols function to solubilize PCMX in aqueous solutions. Suitable alcohols include isopropanol. Suitable glycols include propylene glycol. When an alcohol is used it is preferably present in a concentration of from about 0.5% w/w to about 1% w/w, about 0.6% w/w to about 0.8% w/w, or about 0.7% w/w to about 0.9% w/w. When a glycol is used it is preferably present in a concentration of from about 0.05% w/w to about 3% w/w, about 1.5% w/w to about 3% w/w, or about 1.5% w/w to about 2.5% w/w.

The balance of the % w/w of the antimicrobial composition is water.

In a particularly preferred embodiment, the antimicrobial composition includes an amine-free enhanced synergistically effective antimicrobial mixture of PCMX, carboxylic acid, glycerol, isopropanol, and sodium dodecyl sulfate. This particular composition is shown in the Examples section to exhibit substantial antimicrobial synergy compared to control samples that contain either carboxylic acid or PCMX. In this embodiment, the concentration of PCMX is about 1% to about 3% w/w, the concentration of carboxylic acid is about 0.1% to about 0.3% w/w, the concentration of glycerol is about 0.01% to about 0.2% w/w, the concentration of isopropanol is about 0.6% w/w to about 0.9% w/w, and the concentration of sodium dodecyl sulfate is about 0.5% to about 3% w/w. In an even more particular embodiment, the concentration of PCMX is about 2% w/w and the concentration of the carboxylic acid is about 0.2% w/w. Water is typically about 94% w/w to about 97% w/w of the composition.

Note that variations in the type and concentrations of additional ingredients are possible provided that the combination does not diminish the synergy between PCMX and carboxylic acid, does not irritate the skin, and does not leave residue that would adversely affect electronic components.

The antimicrobial composition is generally prepared by blending the ingredients together with continuous agitation at a controlled temperature. For example, one can first add the desired amount of sodium dodecyl sulfate to distilled, deionized water at about 40° C. with mild agitation to dissolve, then add the carboxylic acid and glycerol to the above solution to the desired concentrations with mild agitation to disperse. If used, the desired amount of poly(oxyethylene) 20 cetyl ether is then added with mild agitation to make it dissolve. The resulting solution is then blended with a solution of PCMX dissolved in a 70% isopropanol/30% water solvent system. The mixture is then agitated until the composition becomes completely transparent.

The antimicrobial composition is preferably used as a rise-free instant hand sanitizer. Accordingly, it may be packaged in dispensing bottles or containers and dispensed onto the hands of a user. It is preferably present in a form that is antimicrobial when applied topically to skin. Suitable forms for topical application include, but are not limited to creams, gels, foams, suspensions, or the like. The antimicrobial composition is particularly useful to sanitize hands in situations where conventional soap and water hand washing facilities are not available or are impractical to use, especially in an electronic component manufacturing facility where it is desireable to avoid contaminating sensitive components with amine residue.

In a preferred method of use aspect of the invention, the antimicrobial composition is used to sanitize the skin of a subject in need thereof by applying an effective amount of the antimicrobial composition to the subject. Here, an "effective amount" is an amount that is sufficient to affect a microbe, such as by inhibiting microbial growth or killing the microbe.

In practice, the subject may dispense the antimicrobial composition onto the subject's hands and rub the hands together.

In another preferred method of use aspect of the invention, a method of preventing interference with electronic components from residue of an electronics worker's hands is provided. The method includes the steps of topically treating the electronics worker's hands with an amine-free enhanced synergistically effective antimicrobial mixture of PCMX, carboxylic acid, glycerol, isopropanol, and sodium dodecyl sulfate and, subsequently, grasping the electronic components with the treated hands. Treating the worker's hands may be accomplished by any conventional means for dispersing a hand sanitizer onto the hands such as by dispensing the composition onto the hands from a container and rubbing the composition onto the hands.

In yet another method of use aspect of the invention, a method of increasing the antimicrobial effectiveness of an amine-free sanitizing solution having PCMX as an antimicrobial active ingredient is provided. The method generally involves blending a carboxylic acid with the sanitizing solution having PCMX as an antimicrobial active ingredient to a ratio of about 30:1 to about 3:1 of PCMX:carboxylic acid, wherein the carboxylic acid synergizes with PCMX in such a way that the antimicrobial effectiveness of the PCMX and carboxylic acid blend is enhanced relative to the sum of antimicrobial effectiveness measurements of PCMX and carboxylic acid when one is measured in the absence of the other. This particular ratio is achieved when the concentration of PCMX is about 1% w/w to about 3% w/w and the concentration of carboxylic acid is about 0.1% w/w to about 0.3% w/w.

EXAMPLES

The following examples are provided for the purpose of illustration and do not limit the scope of the invention in any way.

Example 1

Antimicrobial Effectiveness Testing

This example shows how the antimicrobial effectiveness of the antimicrobial composition was tested and describes the unexpected result that the PCMX and carboxylic acid in the composition synergistically enhances the antimicrobial effectives when compared to the antimicrobial effectiveness of each of these tested individually.

For these tests, ten samples of the antimicrobial composition were prepared. The ingredients of each sample are shown in Table 1 as % w/w. SDS means sodium dodecyl sulfate. The concentration of water was the remaining balance of the % w/w for each.

TABLE 1

| | Samples used for antimicrobial testing | | | | | | | | | |
|---|---|---|---|---|---|---|---|---|---|---|
| Component | 1 | 2 | 3 | 4 | 5 | 6 | 7 | 8 | 9 | 10 |
| PCMX | — | 2 | — | 2 | 2 | 2 | 2 | — | — | — |
| SDS | 2 | 2 | 2 | 2 | 2 | 2 | 2 | 2 | 2 | 2 |
| Glycerol | 0.1 | 0.1 | 0.1 | 0.1 | 0.1 | 0.1 | 0.1 | 0.1 | 0.1 | 0.1 |
| Propylene glycol | 0.2 | 0.2 | 0.2 | 0.2 | 0.2 | 0.2 | 0.2 | 0.2 | 0.2 | 0.2 |
| Isopropanol | 0.8 | 0.8 | 0.8 | 0.8 | 0.8 | 0.8 | 0.8 | 0.8 | 0.8 | 0.8 |
| Benzoic acid | — | 0.2 | 0.2 | — | — | — | — | — | — | — |
| Citric acid | — | — | — | — | 0.2 | — | — | 0.2 | — | — |

TABLE 1-continued

Samples used for antimicrobial testing

| Component | 1 | 2 | 3 | 4 | 5 | 6 | 7 | 8 | 9 | 10 |
|---|---|---|---|---|---|---|---|---|---|---|
| Salicylic acid | — | — | — | — | — | — | 0.2 | — | — | 0.2 |
| Acetic acid | — | — | — | — | — | 0.2 | — | — | 0.2 | — |
| Water | qs | qs | qs | qs | qs | qs | qs | qs | qs | qs |

Minimum inhibitory concentration (MIC) studies were performed using the gram-negative enterobacterium *Escherichia coli* (*E. coli*; American Type Culture Collection #48394) in accordance with the protocol for testing the bactericidal activity of antimicrobial agents (Document M26-T of the National Center for Clinical and Laboratory Standards). *E. coli* cultures were passaged for consecutive daily passages in trypsin soy broth to insure that microorganisms were in log-growth phase. *E. coli* were then subcultured for 8 hours at 37° C. in trypsin soy broth to a final density of approximately $1 \times 10^8$ colony forming units/milliliter (0.5 McFarland nephelometric standard) and then diluted 1:10 with cation-adjusted Mueller-Hinton medium. 50 microliters of this bacterial culture was then added to 500 microliters of an already-prepared dilution series of the test antimicrobial solution (Compositions 1-10 of Table 1) in triplicate. After a 30 second incubation at room temperature, 1000 microliters of Letheen Broth was added to the test solutions. Neutralization of antimicrobial actives in the compositions being tested by this latter procedure was verified by lack of inhibition of *E. coli* growth in a combination of 500 microliters of Composition 4 treated with 1000 microliters of Letheen Broth prior to inoculation with 50 microliters of the standard *E. coli* bacterial culture.

Cultures were incubated for 48 hours at 37° C. before MIC breakpoints were scored. MIC breakpoints were interpreted as the highest dilution for which no growth was evident.

The results shown in Table 2 and FIG. 1 indicate that the compositions that include PCMX and carboxylic acid have an antimicrobial effectiveness that is synergistic. The synergistic effect is most pronounced between composition 2 and 7, suggesting that salicylic acid and benzoic acid are particularly advantageous for use as the carboxylic acid. The synergy observed was significant and unexpected, however, for all of the carboxylic acids tested.

TABLE 2

Antimicrobial performance of the compositions of Table 1 against *E. coli*.
MIC Breakpoint (triplicates)

| Composition | 0 | 1/2 | 1/4 | 1/8 | 1/16 | 1/32 | 1/64 | 1/128 | 1/256 |
|---|---|---|---|---|---|---|---|---|---|
| 1  | —,—,— | —,—,— | +++ | +++ | +++ | +++ | +++ | +++ | +++ |
| 2  | —,—,— | —,—,— | —,—,— | —,—,— | —,—,— | —,—,— | —,—,— | —,—,— | +++ |
| 3  | —,—,— | —,—,— | +++ | +++ | +++ | +++ | +++ | +++ | +++ |
| 4  | —,—,— | —,—,— | —,—,— | —,—,— | —,—,— | +++ | +++ | +++ | +++ |
| 5  | —,—,— | —,—,— | —,—,— | —,—,— | —,—,— | —,—,— | —,—,— | +++ | +++ |
| 6  | —,—,— | —,—,— | —,—,— | —,—,— | —,—,— | —,—,— | —,—,— | +++ | +++ |
| 7  | —,—,— | —,—,— | —,—,— | —,—,— | —,—,— | —,—,— | —,—,— | —,—,— | —,—,— |
| 8  | —,—,— | —,—,— | +++ | +++ | +++ | +++ | +++ | +++ | +++ |
| 9  | —,—,— | —,—,— | +++ | +++ | +++ | +++ | +++ | +++ | +++ |
| 10 | —,—,— | —,—,— | +++ | +++ | +++ | +++ | +++ | +++ | +++ |

(—: Culture negative for growth; +: Culture positive for growth)
The fractions represent dilution rates The invention has been described above with reference to preferred embodiments. Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described. However, the skilled should understand that the methods and materials used and described are examples and may not be the only ones suitable for use in the invention.

Moreover, it should also be understood that any temperature, weight, volume, time interval, pH, salinity, molarity or molality, range, concentration and any other measurements, quantities or numerical figures expressed herein are intended to be approximate and not an exact or critical figure unless expressly stated to the contrary. In addition, as noted above, materials, methods and examples given are illustrative in nature only and not intended to be limiting.

The invention has been described in some detail, but it will be apparent that various modifications and changes can be made within the spirit and scope of the invention as described in the foregoing specification and in the appended claims.

That which is claimed is:

1. An antimicrobial composition comprising:
   parachlorometaxylenol (PCMX) in an amount of 1.0% w/w to 3.0% w/w;
   carboxylic acid in an amount of 0.1% w/w to 0.3% w/w;
   glycerol in an amount of 0.01% w/w to 0.2% w/w;
   isopropanol in an amount of 0.6% w/w to 0.9% w/w;
   sodium dodecyl sulfate in an amount of 0.5% w/w to 3.0% w/w; and
   water wherein said carboxylic acid is selected from benzoic acid or salicylic acid.

2. The composition of claim 1, wherein the carboxylic acid is selected from the group consisting of citric acid, acetic acid, salicylic acid, benzoic acid, and a combination thereof.

3. The composition of claim 1, wherein the carboxylic acid comprises salicylic acid.

* * * * *